(12) United States Patent
Arce

(10) Patent No.: US 9,878,529 B2
(45) Date of Patent: Jan. 30, 2018

(54) ADHESIVE DISPOSABLE CONTAINER

(71) Applicant: Charlotte Arce, Schiller Park, IL (US)

(72) Inventor: Charlotte Arce, Schiller Park, IL (US)

(*) Notice: Subject to any disclaimer, the term of this patent is extended or adjusted under 35 U.S.C. 154(b) by 0 days.

(21) Appl. No.: 14/543,497

(22) Filed: Nov. 17, 2014

(65) Prior Publication Data

US 2015/0158634 A1 Jun. 11, 2015

Related U.S. Application Data

(60) Provisional application No. 61/913,751, filed on Dec. 9, 2013.

(51) Int. Cl.
*B65D 85/62* (2006.01)
*B32B 37/18* (2006.01)
(Continued)

(52) U.S. Cl.
CPC .............. *B32B 37/18* (2013.01); *A01M 29/12* (2013.01); *A47G 19/03* (2013.01); *B65D 21/0227* (2013.01); *B65D 69/00* (2013.01); *B65D 85/62* (2013.01); *A61L 2/23* (2013.01); *A61L 9/12* (2013.01); *B29C 65/4825* (2013.01); *B29C 65/76* (2013.01); *B29C 66/1122* (2013.01); *B29C 66/21* (2013.01); *B29C 66/543* (2013.01); *B29C 66/545* (2013.01); *B29L 2031/712* (2013.01); *Y10T 156/10* (2015.01)

(58) Field of Classification Search
CPC ........ A47G 19/00; A47G 19/02; A47G 19/03; A47G 19/06; A47G 19/08; A47G 19/10; B29C 65/4825; B29C 65/76; B65D 21/0227; B65D 25/00; B65D 25/20; B65D 69/00; B65D 85/62; B65D 77/00; B65D 77/003; B65D 77/02; B65D 81/34; B65D 85/70; A61N 65/00
USPC ......... 206/460, 515–520, 813; 220/574–575; 229/406, 407
See application file for complete search history.

(56) References Cited

U.S. PATENT DOCUMENTS 2,647,678 A 8/1953 Olson
3,847,324 A * 11/1974 Uchanski ............... A47G 19/03
206/813

(Continued)

FOREIGN PATENT DOCUMENTS

EP 0 557 252 A1 8/1993
EP 0 532 233 B1 4/1996
(Continued)

OTHER PUBLICATIONS

"Bugables® Mesquito Repellent Stickers" (downloaded Oct. 2014).
(Continued)

*Primary Examiner* — Bryon Gehman
(74) *Attorney, Agent, or Firm* — Husch Blackwell LLP

(57) ABSTRACT

The invention relates to a disposable container for holding food or for decorative purposes. The disposable container has a surface with an adhesive layer to removably detach the disposable container from the surface of another disposable container, to form a stacked configuration with multiple disposable containers. The disposable container can also contain a fragrance or non-toxic insect repellent on a surface or in the adhesive layer, which can release the fragrance or non-toxic insect repellent.

11 Claims, 4 Drawing Sheets

(51) Int. Cl.
*B65D 21/02* (2006.01)
*A47G 19/03* (2006.01)
*A01M 29/12* (2011.01)
*B65D 69/00* (2006.01)
*A61L 9/12* (2006.01)
*A61L 2/23* (2006.01)
*B29L 31/00* (2006.01)
*B29C 65/48* (2006.01)
*B29C 65/76* (2006.01)
*B29C 65/00* (2006.01)

(56) References Cited

U.S. PATENT DOCUMENTS

| | | | | |
|---|---|---|---|---|
| 4,530,867 A * | 7/1985 | Gorman | ............... | A47G 19/03 428/198 |
| 5,009,310 A * | 4/1991 | Finney | ............... | B65D 25/20 426/115 |
| 5,236,119 A | 8/1993 | Chu | | |
| 5,688,509 A * | 11/1997 | Radwan et al. | ....... | A61N 65/00 424/195.1 |
| 6,561,375 B1 * | 5/2003 | Nagy | ............... | A47G 19/02 206/460 |
| 6,578,499 B2 * | 6/2003 | Kroll | ............... | A47G 19/10 108/90 |
| 7,552,840 B2 | 6/2009 | Gitschlag et al. | | |
| 7,749,525 B2 * | 7/2010 | Navarro et al. | ....... | A61N 25/32 424/403 |
| 8,292,342 B2 | 10/2012 | Lord | | |
| 8,968,647 B2 * | 3/2015 | Fischer | ............... | A61L 9/12 206/484 |
| 9,101,143 B2 * | 8/2015 | Markus et al. | ....... | A61N 65/00 |
| 9,107,522 B1 * | 8/2015 | Mauck | ............... | A47G 19/03 |
| 2001/0007325 A1 * | 7/2001 | Kroll | ............... | A47G 19/10 220/574 |
| 2003/0201271 A1 * | 10/2003 | Smith | ............... | A47G 19/08 220/574 |
| 2006/0198861 A1 * | 9/2006 | Villers | ............... | B65D 81/24 383/113 |
| 2008/0060739 A1 * | 3/2008 | Collins | ............... | B65D 25/20 156/60 |
| 2008/0060966 A1 * | 3/2008 | Collins | ............... | B65D 21/0205 206/508 |
| 2012/0248124 A1 | 10/2012 | Mitri et al. | | |
| 2013/0029075 A1 | 1/2013 | Niiyama et al. | | |

FOREIGN PATENT DOCUMENTS

| | | |
|---|---|---|
| EP | 0 597 999 B1 | 11/1996 |
| EP | 1 072 521 A2 | 1/2001 |
| EP | 1 881 894 A1 | 1/2008 |
| EP | 1 654 129 B1 | 5/2008 |
| EP | 1 993 918 B1 | 7/2011 |
| WO | WO 2007/047619 A2 | 4/2007 |

OTHER PUBLICATIONS

"Edible Insect Repellent" (downloaded 2014).
"Organis The Healthy and Safe Natural Insect Repellent Platform" (Misgav Venture Accelerator 2012).
"Trendlines Organis" (available at http://trendlines.com/portfolio/organis/ on Oct. 21, 2014).
"Neat Solutions Table Topper" (Neat Solutions 2012) (available at http://www.tabletopper.com/product/table_toppers).

* cited by examiner

ADHESIVE DISPOSABLE CONTAINER

The present application claims the benefit of the filing date of U.S. provisional application Ser. No. 61/913,751, filed 9 Dec. 2013.

This invention pertains to adhesive disposable containers for holding food or for decorative purposes.

BRIEF DESCRIPTION OF THE DRAWINGS

The following drawings illustrate the concepts of the present invention, and are not necessarily drawn to scale.

DETAILED DESCRIPTION OF SOME EMBODIMENTS

Figure 1:
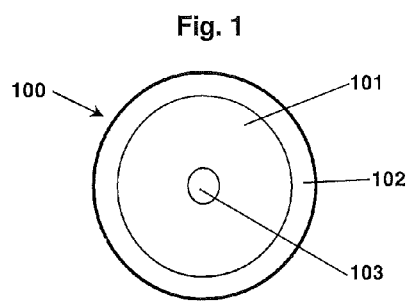
FIG. 1 is a bottom view of an embodiment of an adhesive disposable container.

While the present invention is susceptible of embodiment in various forms, there is shown in the drawings and will hereinafter be described some embodiments with the understanding that the present disclosure is to be considered an exemplification of the invention and is not intended to limit the invention to the specific embodiments illustrated.

Disposable containers may be used, for example, for serving food or for decorative purposes. Drawing on a paper plate and attaching it to a wall is an example of such a decorative purpose. A common use of disposable containers is for holding food outdoors, where they are prone to getting blown off of a picnic table, for example. A disposable container with an adhesive layer reduces the likelihood of the container being blown away from where it was intended to be located, and facilitates using the disposable container for decorative purposes. A disposable container with an adhesive layer also may be used for pets, where the adhesive layer reduces the likelihood of the container being moved while the pet attempts to eat from the container.

FIG. 1 is a bottom view of an embodiment of an adhesive disposable container 100. It includes a generally planar bottom section 101 having a generally flat bottom surface, and an extension section 102 generally surrounding and extending outwardly from the bottom section 101. It also includes at least one adhesive layer 103 that is joined to the bottom surface 101, and that is structured and dimensioned for releasably attaching the container 100 to objects or surfaces. For example, the adhesive is physically bonding, solvent-free, pressure sensitive and adhesive at room-temperature. It also can be edible, and might serve as a non-toxic insect repellent.

Being disposable, container 100 may made, for example, of contoured paper board, of an expanded polystyrene foam or of another plastic material, or of any material used in the disposable container industry. It may be manufactured, for example, by thermoforming a plastic material such as polyethylene or polypropylene. It may, for example, be made of a filled plastic, that may, for example, comprise a mineral filler such as mica, talc, kaolin, glass fiber, silica, silicon carbide whiskers, or some mixture of them. As another variation, manufacture of container 100 may include applying non-toxic insect repellent, such as turmeric, lemon grass, or another edible plant-based insect repellent. Organis is a company that has developed an insect repellent derived from the edible turmeric plant, and has partnered with other companies to market aerosols and packaging materials using that non-toxic insect repellent.

Figure 2:
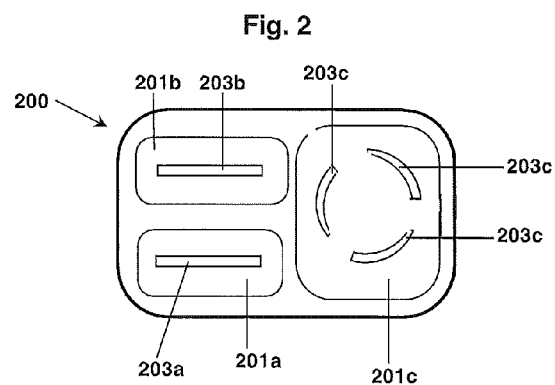
FIG. 2 is a bottom view of another embodiment of an adhesive disposable container.

While container 100 illustrated in FIG. 1 is a plate, an adhesive disposable container can, for example be a bowl, a cup, a tray, a container that is compartmentalized into multiple sections, and so forth. For example, FIG. 2 illustrates a bottom view of an embodiment of an adhesive disposable container 200 that has multiple bottom sections 201a, 201b and 201c.

The at least one adhesive layer can include releasably adhesive sections of any shape. For example, the adhesive layer 103 shown in FIG. 1 is circular. The adhesive layers 203a and 203b shown in FIG. 2 are rectilinear. The adhesive layers 203c shown in FIG. 2 are arc-shaped. The adhesive layer also could be X-shaped, crescent-shaped, and so forth. The at least one adhesive layer can be located in different places on the bottom surface. For example, the adhesive layer 103 shown in FIG. 1 is in the center of bottom section 101, and the adhesive layers 203a and 203b shown in FIG. 2 are in the center of bottom sections 201a and 201b, respectively. However, the adhesive layers 203c shown in FIG. 2 are near the periphery of bottom section 201c.

Figure 7:
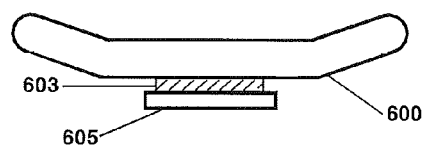
FIG. 7 is a cross-sectional side view of an embodiment of an adhesive disposable container with a strippable protective layer covering the adhesive layer.

In some embodiments, the at least one adhesive layer can be covered with a strippable protective layer that may preserve a releasably adhesive section of the adhesive layer for a prolonged duration. For example, FIG. 7 is a cross-sectional side view of disposable container 600 with an adhesive layer 603 that is covered with a strippable protective layer 605.

Figure 11:
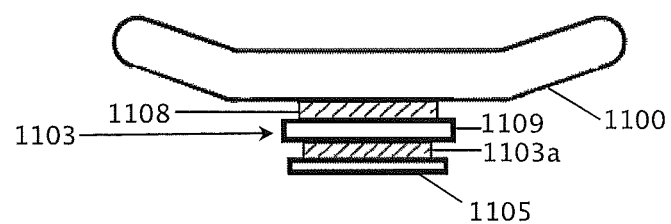
FIG. 11 is a cross-sectional side view of an embodiment of an adhesive disposable container, with the adhesive layer comprising a connection layer that is permanently bonded on one face and a releasably adhesive section on the opposite face, and with a strippable protective layer covering the releasably adhesive section.

In some embodiments, the adhesive layer comprises a connection layer and a releasably adhesive section. In those embodiments, one face of the connection layer is bonded to or fastened to the bottom surface of the disposable container, such as with a permanent rubber-based adhesive, and the releasably adhesive section is joined to the opposite face of the connection layer for releasably attaching the container to objects or surfaces. For example, FIG. 11 is a cross-sectional side view of an embodiment of an adhesive disposable container 1100. The adhesive layer 1103 comprises a connection layer 1109 and a releasably adhesive section 1103a. One face of the connection layer 1109 is permanently bonded via bonding material 1108, and the releasably adhesive section 1103*a* is on the opposite face of the connection layer 1109. The releasably adhesive section 1103*a* is covered with a strippable protective layer 1105. One example of manufacturing this embodiment is to apply a commercially available connection layer to a disposable container. For example, commercially available Remo One® pre-cut pieces have a permanent adhesive on one side and a releasable adhesive on the other side.

In some embodiments, a plurality of the disposable containers can be packaged together with a plurality of sealed packets, where each of the sealed packets contains a sanitizing agent. The sanitizing agent may be, for example, a gel, a liquid, a powder, a multi-purpose skin solution, a tissue, or an antibacterial wipe. Packaging material can surround the plurality disposable containers and the plurality of sealed packets, and can be sealed to create a single package.

Figure 3:
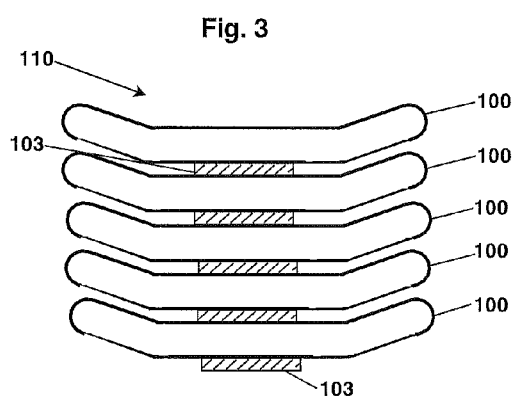
FIG. 3 is a cross-sectional side view of a stack of containers like the container shown in FIG. 1.

In some embodiments, the disposable containers can be stacked, and the stacked containers are releasably held together by the adhesive layers of the respective containers. For example, FIG. 3 is a cross-sectional side view of a stack 110 of containers 100. Upon removing a top container 100 from the stack, an adhesive layer 103 joined to the bottom surface of that top container 100 is exposed and that top container 100 can be releasably attached to another object or surface.

Figure 8:
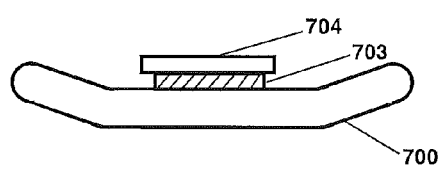
FIG. 8 is a cross-sectional side view of an embodiment of an adhesive disposable container with a sealed packet containing a sanitizing agent adhered to the container.

In some embodiments, the adhesive layer may be on any surface of the container, and is used at least to join a sealed packet containing a sanitizing agent to the container. For example, FIG. 8 is a cross-sectional side view of disposable container 700 joined to packet 704 by adhesive layer 703. In these embodiments, a sealed packet 704 also is a strippable protective layer and, in addition to containing a sanitizing agent, also serves the function served by a strippable protective layer 605 in the example of FIG. 7.

In some embodiments, a sanitizing agent may be interspersed between each of the containers in a stack of adhesive disposable containers. The sanitizing agents may be contained in sealed packets such as a packet with a peelable membrane, or the stacking of the containers may form sealed spaces for the sanitizing agents.

Figure 4:
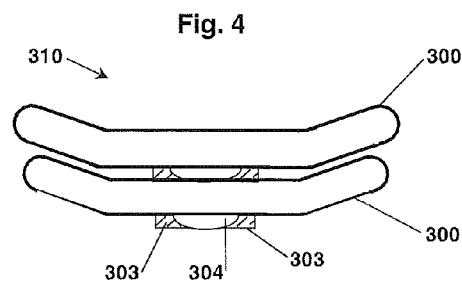
FIG. 4 is a cross-sectional side view of one embodiment of two stacked adhesive disposable containers with a sanitizing agent interspersed between them.
Figure 5:
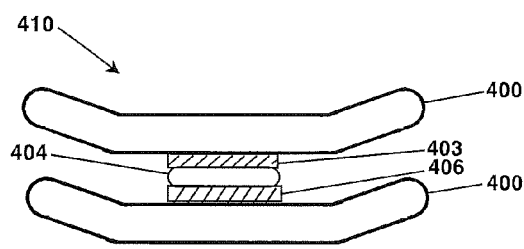
FIG. 5 is a cross-sectional side view of another embodiment of two stacked adhesive disposable containers with a sanitizing agent interspersed between them.
Figure 6:
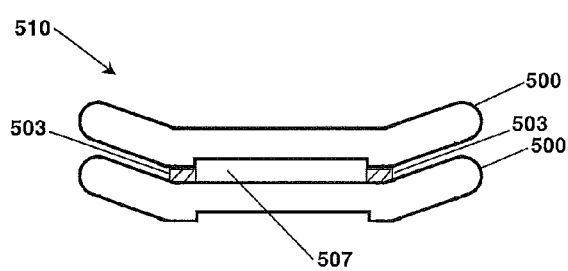
FIG. 6 is a cross-sectional side view of another embodiment of two stacked adhesive disposable containers with a sanitizing agent interspersed between them.

For example, FIG. 4 is a cross-sectional side view of a stack 310 of two adhesive disposable containers 300, with a sanitizing agent sealed packet 304 between them. In the illustrated embodiment, at least part of the adhesive layer 303 is directly in contact with adjacent containers 300. Illustrating a different embodiment, FIG. 5 is cross-sectional side view of a stack 410 of two adhesive disposable containers 400, with a sanitizing agent sealed packet 404 between them. Adhesive layer 403 joins the bottom of the top container to the top of packet 404, and additional adhesive layer 406 joins the top of the bottom container to the bottom of packet 404. Illustrating a different embodiment, FIG. 6 is a cross-sectional side view of a stack 510 of two adhesive disposable containers 500, with a sanitizing agent 507 between them. No separate sealed packet is necessary because the containers 500 and the adhesive layer 503 form a sealed space for the sanitizing agent 507.

Figure 9:
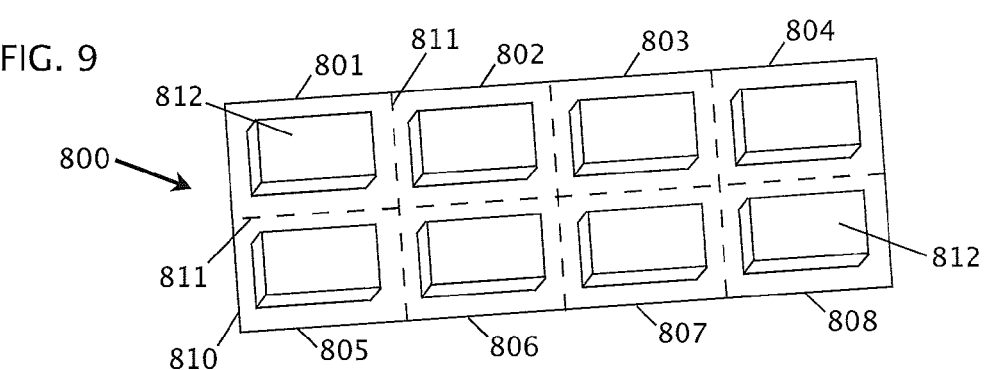
FIG. 9 is a bottom perspective view of an embodiment of the multi-unit package.
Figure 10:
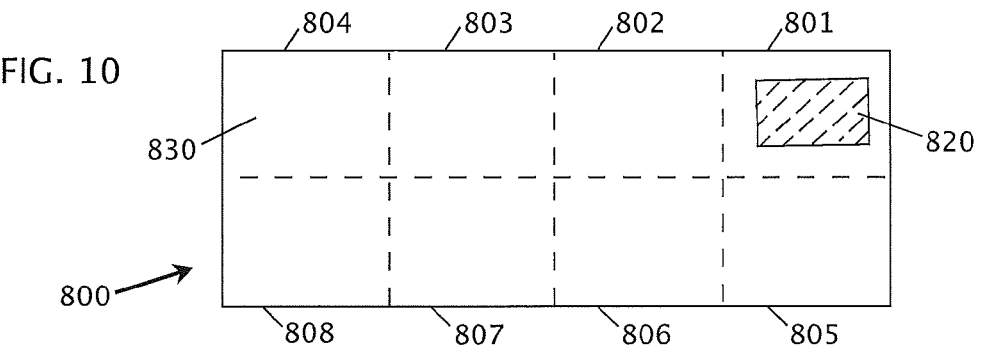
FIG. 10 is a top view of the embodiment of FIG. 9 with a seal removed from one of the units.

FIGS. 9 and 10 illustrate an embodiment of a disposable multi-unit package 800 of sanitizing agents that may be included with a stack of adhesive plates, or that may stand alone. FIG. 9 is a bottom perspective view of an embodiment of the multi-unit package 800. It comprises a shell 810 with a plurality of units 801-808 separated from each other by perforations 811 to facilitate removal of a single unit from the multi-unit package 800. Each unit includes a cavity 812 for storing a sanitizing agent 820. FIG. 10 is a top view of the embodiment of FIG. 9. It shows that each of the cavities 812 is sealed by a removable seal 830, such as a strippable or breakable paper, plastic or foil, that is sealed to the shell 810 by an adhesive. In FIG. 10, the seal 830 has been removed from unit 801, one of the units of multi-unit package 800, exposing sanitizing agent 820. While each cavity 812 is substantially rectilinear in the example of FIGS. 9 and 10, the cavities may form any shape such as circular or arc-shaped, for example.

In the example of FIGS. 9 and 10, each unit 801-808 of the multi-unit package 800 stores an amount of sanitizing agent 820 appropriate for a single use. The sanitizing agent 820 may be, for example, a liquid, a gel, a powder, or a multi-purpose skin solution. A common use of the multi-unit package 800 involves separating a single unit (801-808) from the multi-unit package 800 along the perforations 811, and stripping away or breaking a seal 830 to expose a cavity 812 containing the sanitizing agent 820.

Being disposable, the shell 810 may be made, for example, of paperboard, pre-formed plastic materials such as polyvinyl chloride (PVC), polychlorotrifluoroethylene (PCTFE), cyclic olefin copolymers (COC) and cyclic olefin polymer (COP), or semicrystalline resins such as polypropylene (PP) and polyethylene (PE). It may be made, for example, of a thermoformed plastic film or sheet, which may be manufactured via coextrusion or lamination.

The multi-unit package 800 may be created, for example, by a form-fill-seal process, which includes rolls of flat sheet or film being filled with a sanitizing agent and sealed shut in either rotary or flat-plate equipment.

In some embodiments, a fragrance is released when the adhesive layer of the container is exposed or when a seal is stripped from a unit of a multi-unit package. For example, this can occur when the strippable protective layer 605 is removed in the illustration of FIG. 7, when the strippable protective layer 1105 is removed in the illustration of FIG. 11, when the sealed packet 704 is removed from the surface of container 700 in the illustration of FIG. 8, when a container is removed from the plurality of stacked containers in any of the illustrations of FIGS. 3-6, or when a seal is removed from a unit of a multi-unit package in the illustrations of FIGS. 9 and 10. The fragrance may constitute the aroma of a perfume or of a food flavor such as strawberry, banana, grape, orange, vanilla, etc. The fragrance may result, for example, from chemicals in the adhesive, in the sanitizing agent, or in both. The fragrance also may be a non-toxic insect repellent. For example, the adhesive may comprise a non-toxic insect repellent, such as turmeric, lemon grass, or another edible plant-based insect repellent as discussed above. In an example of a multi-unit package illustrated in FIGS. 9 and 10, the fragrance of at least one unit, or possibly every unit, of the multi-unit package may be different than the fragrance of the other units of the multi-unit package.

From the foregoing, it will be understood that numerous modifications and variations can be effectuated without departing from the true spirit and scope of the novel concepts of the present invention. It is to be understood that no limitation with respect to the specific embodiments illustrated is intended or should be inferred.

What is claimed is:

1. A disposable container for holding food or for decorative purposes, comprising:
   a generally planar bottom section, having a generally flat bottom surface;
   an extension section generally surrounding and extending outwardly from the bottom section; and at least one solvent-free, edible plant-based insect-repellent-containing releasable-at-room temperature pressure-sensitive adhesive layer containing one first face and an opposite second face where the first face of the adhesive layer is joined to the exterior surface of the bottom surface of the container, the second face has a strippable protective layer preserving a releasably adhesive section of the second face for a prolonged duration, the at least one adhesive layer being structured and dimensioned for releasably attaching the container to objects or surfaces.

2. The container of claim 1 wherein the container is selected from a group consisting of a plate, a bowl, a cup, a tray, and a container that is compartmentalized into multiple sections.

3. The container of claim 1 wherein a shape of the at least one adhesive layer is selected from a group consisting of substantially circular, substantially rectilinear, and substantially arc-shaped.

4. The container of claim 1 wherein a location of the at least one adhesive layer is selected from a group consisting of: generally in a center of the bottom section, and generally near a periphery of the bottom section.

5. A plurality of stacked containers, each of the plurality of stacked containers being a container as in claim 1, wherein the plurality of stacked containers are releasably held together by the at least one adhesive layer of the respective containers.

6. A process for producing a disposable container having a solvent-free edible plant-based insect repellent, for holding food or for decorative purposes, the process comprising:
providing the container having a generally flat bottom surface with an extension section generally surrounding and extending outwardly from the bottom section; and
joining at least one solvent-free, edible plant-based insect repellent-containing, releasable-at-room temperature pressure sensitive adhesive layer to an external surface of the bottom surface, the at least one adhesive layer being structured and dimensioned for releasably attaching the container to objects or surfaces;
wherein the at least one adhesive layer has a strippable protective layer where the strippable protective layer preserves a releasably adhesive pressure-sensitive section of the adhesive layer for a prolonged duration.

7. A disposable container for holding food or for decorative purposes, comprising:
a generally planar bottom section, having a generally flat bottom surface;
an extension section generally surrounding and extending outwardly from the bottom section;
at least one solvent-free non-toxic insect-repellent, releasable-at-room temperature pressure sensitive adhesive layer component, one joined to an exterior surface of the bottom surface, the at least one component, one adhesive layer being structured and dimensioned for releasably attaching the container to objects or surfaces;
the at least one adhesive layer comprises a releasable adhesive section that is physically bonding, and
wherein the at least one adhesive layer has a strippable protective layer where the strippable protective layer preserves a portion of the at least one adhesive layer for a prolonged duration.

8. The container of claim 7 wherein a shape of the releasably adhesive portion of the at least one adhesive layer is selected from a group consisting of substantially circular, substantially rectilinear, and substantially arc-shaped.

9. The container of claim 7 wherein a location of the at least one adhesive layer is selected from a group consisting of: generally in a center of the bottom section, and generally near a periphery of the bottom section.

10. The container of claim 7 wherein the solvent-free non-toxic insect repellent is edible.

11. A plurality of stacked containers, each of the plurality of stacked containers being a container as in claim 7, wherein the plurality of stacked containers are releasably held together by the at least one adhesive layer of the respective containers.

* * * * *